(12) United States Patent
De Vries et al.

(10) Patent No.: US 10,106,821 B2
(45) Date of Patent: Oct. 23, 2018

(54) METHOD FOR PROCESSING MAGNESIUM CHLORIDE SOLUTIONS

(71) Applicant: PURAC BIOCHEM B.V., Gorinchem (NL)

(72) Inventors: Johannes Jeichienus De Vries, Gorinchem (NL); Raymon Frediansyah, Gorinchem (NL); André Banier De Haan, Gorinchem (NL)

(73) Assignee: PURAC BIOCHEM B.V., Gorinchem (NL)

( * ) Notice: Subject to any disclaimer, the term of this patent is extended or adjusted under 35 U.S.C. 154(b) by 86 days.

(21) Appl. No.: 14/902,374

(22) PCT Filed: Jul. 2, 2014

(86) PCT No.: PCT/EP2014/064059
§ 371 (c)(1),
(2) Date: Dec. 31, 2015

(87) PCT Pub. No.: WO2015/000956
PCT Pub. Date: Jan. 8, 2015

(65) Prior Publication Data
US 2016/0369302 A1 Dec. 22, 2016

(30) Foreign Application Priority Data
Jul. 3, 2013 (EP) .................................... 13174834

(51) Int. Cl.
*C12P 3/00* (2006.01)
*C01F 5/10* (2006.01)
(Continued)

(52) U.S. Cl.
CPC .................................... *C12P 3/00* (2013.01);
*C01B 7/01* (2013.01); *C01B 7/035* (2013.01);
*C01F 5/10* (2013.01);
(Continued)

(58) Field of Classification Search
CPC ........... C12P 3/00; C12P 7/40; C12P 2006/80;
C01F 5/10; C01F 5/30; C01B 7/035;
C01B 5/30; C01B 7/01
See application file for complete search history.

(56) References Cited

FOREIGN PATENT DOCUMENTS

CN 101796194 A 8/2010
EP 2175033 A1 4/2010
(Continued)

OTHER PUBLICATIONS

Jedlicka; "Production of Magnesia (+ 99% MgO) by the Ruthner-HCl-Route;" publication date unknown to Applicant; Published by Andritz-Ruthner Industrieaniagen Aktiengesellschaft; Vienna, Austria.

(Continued)

*Primary Examiner* — James A Fiorito
(74) *Attorney, Agent, or Firm* — Oliff PLC

(57) ABSTRACT

A method for processing $MgCl_2$ solutions including the steps of: providing an aqueous solution including 5-25 wt. % of $MgCl_2$ and optionally organic contaminants to a step, wherein water and present, organic components are evaporated; withdrawing aqueous solution with a $MgCl_2$ concentration of 25-35 wt. % from an evaporation step and providing it to a preconcentrator where it is contacted with a HCl containing gas stream at least 300° C.; providing aqueous solution with a $MgCl_2$ concentration of 35-45 wt. % resulting from the preconcentrator to a thermohydrolysis reactor, being at at least 300° C.; withdrawing MgO from the thermohydrolysis reactor in solid form, and withdrawing a HCl containing gas stream from the thermohydrolysis reactor, said HCl-containing gas stream at least 300° C.; providing the HCl-containing gas stream with at least 300° C.

(Continued)

to the preconcentrator; withdrawing a HCl-containing gas stream with a temperature of at most 150° C. from the preconcentrator.

16 Claims, 2 Drawing Sheets

(51) Int. Cl.
    *C12P 7/40*     (2006.01)
    *C01F 5/30*     (2006.01)
    *C01B 7/01*     (2006.01)
    *C01B 7/03*     (2006.01)
    *C07C 51/02*     (2006.01)
(52) U.S. Cl.
    CPC ............... *C01F 5/30* (2013.01); *C07C 51/02* (2013.01); *C12P 7/40* (2013.01); *C01P 2006/80* (2013.01)

(56) References Cited

FOREIGN PATENT DOCUMENTS

| EP | 2666763 A1 | * | 11/2013 | ............... C01F 5/10 |
|----|------------|---|---------|---------------------------|
| GB | 2006175 A  |   | 5/1979  |                           |
| RU | 2321541 C2 |   | 4/2008  |                           |
| WO | 00/17378 A2 |  | 3/2000  |                           |
| WO | 2013/025106 A1 | | 2/2013 |                           |

OTHER PUBLICATIONS

Oct. 1, 2014 Search Report issued in International Patent Application No. PCT/EP2014/064059.
Oct. 1, 2014 Written Opinion issued in International Patent Application No. PCT/EP2014/064059.

* cited by examiner

METHOD FOR PROCESSING MAGNESIUM CHLORIDE SOLUTIONS

The present invention pertains to a method for processing magnesium chloride solutions, in particular magnesium chloride solutions derived from the manufacture of organic compounds through fermentation processes.

WO00/17378 describes a method for manufacturing lactic acid, wherein in a fermentation process a magnesium lactate solution is prepared. The magnesium lactate solution is acidified with HCl to yield a solution comprising lactic acid in a magnesium chloride solution. The lactic acid is recovered from the solution. The resulting magnesium chloride solution may be processed by subjecting it to a thermohydrolysis step at a temperature of at least 500° C. to react the magnesium chloride with water to yield magnesium oxide powder and hydrochloric acid. The heat required for the thermohydrolytic reaction is provided by the in situ combustion of fuel. Traces of organic matter are incinerated.

WO2013/025106 describes a method for manufacturing carboxylic acids through a process comprising the steps of acidifying a magnesium salt of a carboxylic acid with HCl to form an acid and a magnesium chloride solution, and isolating the acid from the solution through precipitation. It is indicated that the magnesium chloride solution may be processed through thermal decomposition.

It has been found that there is need in the art for a method for processing magnesium chloride solutions which is suitable for processing solutions derived from a fermentation process while obtaining an efficient and highly stable integrated process.

The present invention pertains to a method for processing MgCl2 solutions comprising the steps of providing an aqueous solution comprising 5-25 wt. % of MgCl2 and optionally organic contaminants to an evaporation step, wherein water and, where present, organic components are evaporated, withdrawing an aqueous solution with a MgCl2 concentration of 25-35 wt. % from an evaporation step and providing it to a preconcentrator where it is contacted with a HCl containing gas stream with a temperature of at least 300° C., providing an aqueous solution with a MgCl2 concentration of 35-45 wt. % resulting from the preconcentrator to a thermohydrolysis reactor, the reactor being at a temperature of at least 300° C., withdrawing MgO from the thermohydrolysis reactor in solid form, and withdrawing a HCl containing gas stream from the thermohydrolysis reactor, said HCl-containing gas stream having a temperature of at least 300° C., providing the HCl-containing gas stream with a temperature of at least 300° C. to the preconcentrator, withdrawing a HCl-containing gas stream with a temperature of at most 150° C. from the preconcentrator.

The following is a brief description of the drawings.

Figure 1:
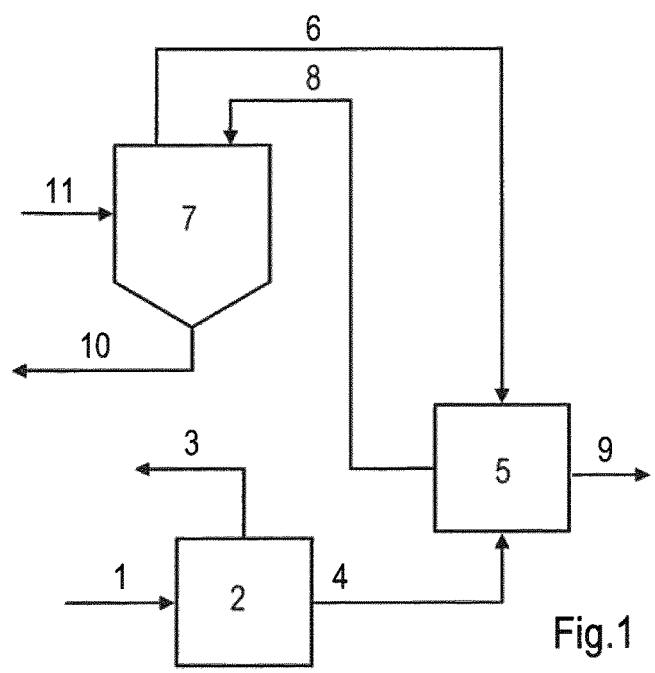
FIG. 1 illustrates the basic steps of the method according to the subject matter of the present application.

It has been found that the process according to the invention can be integrated into a fermentation process in such a manner that a stable and efficient process is obtained.

The present invention will be discussed in more detail below.

The present invention starts out with a the step of providing an aqueous solution comprising 5-25 wt. % of MgCl2 and optionally organic contaminants to an evaporation step, wherein water and, where present, organic components are evaporated.

The starting solution comprising 5-25 wt. % of MgCl2 and optionally organic contaminants is generally derived from the manufacture of organic compounds through fermentation processes. Depending on the nature of process from which the magnesium chloride solution is derived, its concentration can vary between the wide ranges indicated above. In one embodiment, the magnesium chloride solution comprises 10-25 wt. % of MgCl2, or 10-20 wt. % of MgCl2.

The starting solution may or may not comprise organic contaminants. In fact, given the source of the starting material, it is highly likely that the starting material will in fact contain such organic contaminants, and it is a particular feature of the process according to the invention that starting materials containing organic contaminants, in particular relatively volatile organic contaminants, can be processed while a fermentation process in which this process is integrated can be operated stably and efficiently. The nature of the organic contaminants may vary within wide ranges. The starting solution may contain remnants of the organic compounds manufactured through fermentation. The starting solution may also contain remnants of extractants or solvents used in the isolation of the organic compound from the magnesium chloride solution.

In one embodiment, the magnesium chloride solution has a concentration of volatile organic compounds, expressed as VTOC (total volatile organic compounds), of at least 1000 ppm (0.1 wt. %). Volatile organic compounds are defined in the context of this specification as compounds which are more volatile than water under the conditions of the first evaporation step. The wording "more volatile" means that the percentage of volatile component that is evaporated in the first evaporation step is larger than the percentage of water that is evaporated in the first evaporation step.

Depending on the nature of the process the VTOC may be, e.g., at least 0.2 wt. %, or at least 0.5 wt. %, or even at 1.0 wt. %. The maximum value is not critical for the process according to the invention. It will generally be below 5 wt. %, more conventionally below 2.5 wt. %.

In one embodiment, the starting magnesium chloride which is provided to the evaporation step has a total organic compound concentration, expressed as TOC (total organic compounds), of at least 1000 ppm (0.1 wt. %). Depending on the nature of the process the organic compound concentration may be, e.g., at least 0.2 wt. %, or at least 0.5 wt. %, or even at 1.0 wt. %. The maximum value is not critical for the process according to the invention. It will generally be below 5 wt. %, more conventionally below 2.5 wt. %.

The magnesium chloride solution may also contain non-volatile organic compounds, also indicated as NVTOC. The amount of NVTOC can be calculated by subtracting the VTOC from the TOC. It may be preferred for the amount of non-volatile compounds, expressed as NVTOC to be relatively limited, because their presence in the magnesium chloride solution may lead to yield loss in the overall process. In general, NVTOC is less than 2 wt. %, preferably less than 1 wt. %, more preferably less than 0.5 wt. %.

In the evaporation step the solution is concentrated by evaporating water therefrom. If present, volatile organic components are removed. In one embodiment, the process is carried out in such a manner that the product resulting from the evaporation step has a VTOC which is at most 50% of the VTOC of the aqueous solution provided to the first evaporation step, in particular at most 30%, more in particular at most 15%. Depending on the VTOC of the starting solution, the product resulting from the evaporation step which is provided to the preconcentrator preferably has a VTOC of at most 1000 ppm (0.1 wt. %), in particular at most 500 ppm, more in particular at most 200 ppm.

The amount of water that is removed depends on the process conditions applied during the evaporation step, and will be governed by the magnesium chloride concentration of the starting solution, which may be indicated as [MgCl2 start] and the desired magnesium chloride concentration of the product to be provided to the preconcentrator, which may be indicated as [MgCl2 prec].

The concentration increase effected during the evaporation steps before the preconcentrator is [MgCl2 prec]-[MgCl2 start], and generally is between 30 and 5 wt. %. It may be preferred for [MgCl2 prec]-[MgCl2 start] to be between 5 and 20 wt. %, specifically between 5 and 15 wt. %.

The evaporation step of the process according to the invention may be a single-stage evaporation step or a multiple-stage evaporation step.

The use of a multiple-stage evaporation may be preferred in the case that the magnesium chloride contains a substantial amount of organic compounds, as described above. In this case, the use of multiple-stage evaporation allows the operation of a first stage dedicated to the removal of volatile organic components and a relatively limited amount of water, with the bulk amount of water being removed in further evaporation stages. This makes for the production in the first stage of an aqueous liquid having a relatively high concentration of volatile organic compounds as compared to effluent of a single-step evaporation, and this higher concentration makes for more efficient processing of the aqueous liquid containing organic compounds, in particular volatile.

In one embodiment, the evaporation step in the process according to the invention is a multiple-stage evaporation wherein the concentrated product resulting from the first evaporation stage has a VTOC which is at most 50% of the VTOC of the aqueous solution provided to the first evaporation stage, in particular at most 30%, more in particular at most 15%. It is preferred for the concentrated product from the first evaporation stage to have a VTOC of at most 1000 ppm (0.1 wt. %), in particular at most 500 ppm, more in particular at most 200 ppm. It may be preferred within this embodiment for the evaporation to be carried out in such a manner that of the concentration increase effected during the evaporation step ([MgCl2 prec]-[MgCl2 start]) at most 50% is effected during the first evaporation stage, with the remainder being obtained in further evaporation stage. Generally, of the concentration increase during the evaporation step at least 10% is effected during the first evaporation stage.

Where the evaporation step is a multi-stage evaporation step, it may be preferred for it to encompass 2-10 evaporation stages, in particular 2-6 evaporation stages.

The evaporation step may be carried out in various manners. In one embodiment, the evaporation step is a multiple stage evaporation, wherein steam is withdrawn from the first evaporation step and provided as heating liquid to a further evaporation step. Within this embodiment it is preferred for each evaporation stage except the first to be provided with steam from the preceding evaporation stage as heating liquid. In one embodiment, the multiple stage evaporation is carried out in a multiple-effect evaporator. A multiple-effect evaporator comprises a set of evaporation vessels wherein each vessel is operated at a pressure which is below the pressure of the preceding vessel. Because the boiling temperature of water decreases as pressure decreases, the vapor boiled off in one vessel can be used to heat the next, and only the first vessel (at the highest pressure) requires an external source of heat. Multiple-effect evaporators are known in the art and require no further elucidation here.

In one embodiment of the present invention, vapor-compression evaporation is used in the evaporation step in the process according to the invention, or in one or more stages thereof. In vapour compression evaporation, the vapour produced during evaporation is compressed, e.g., using a blower, compressor or jet ejector, to increase the pressure. Since an increase in pressure results in an increase in condensation temperature, the vapour can be recycled as the heating medium for the solution being concentrated, from which the vapor was generated to begin with. This process is sometimes indicated as vapour compression distillation (VCD). Where the compression is performed by mechanical means, the process is sometimes also indicated as mechanical vapour recompression (MVR). Vapour compression evaporation is known in the art and requires no further elucidation here.

In one embodiment of the present invention, where the starting solution comprises organic components as described above, the evaporation step encompasses two evaporation stages, wherein in the first stage a TOC reduction is obtained as described above, with a magnesium chloride concentration increase of at most 50%, in particular at most 30%, more in particular at most 10%, calculated on the total concentration increase ([MgCl2 prec]-[MgCl2 start]), and wherein the second evaporation stage, which effects more than 50% of the total concentration increase, in particular at least 70%, more in particular at least 90%, is a vapour compression evaporation.

The next step in the method according to the invention is providing an aqueous solution with a MgCl2 concentration of 25-35 wt. % from the evaporation step to a preconcentrator where it is contacted with a HCl containing gas stream with a temperature of at least 300° C. By contacting the aqueous solution with the hot gas, a number of effects are obtained. A first effect is that the temperature of the hot HCl-containing gas is decreased from a value of above 300° C. to a value of at most 150° C. A second effect is that water is evaporated, resulting in a further increase of the magnesium chloride concentration to a value of 35-45 wt. %. A further effect which may sometimes occur is that the temperature of the magnesium chloride solution increases to a value of at most 150° C.

The aqueous magnesium chloride solution with a MgCl2 concentration of 35-45 wt. % resulting from the preconcentrator is provided to a thermohydrolysis reactor. In the thermohydrolysis reactor the magnesium chloride reacts with water to form magnesium oxide and HCl.

Suitable apparatuses for conducting the thermohydrolysis also indicated herein as thermal decomposition, are known in the art. For example, a spray roaster or a fluid bed roaster can be used. Such apparatuses can for example be obtained at SMS Siemag, Andritz. Tenova, CMI, and Chemline.

The use of a spray roaster is preferred. A spray roaster has low energy costs (also compared to a fluid bed roaster), because it requires relatively low temperatures (as described below). A spray roaster was further found to produce reactive MgO particles, which are very suitable for use as a neutralizing agent in fermentation. Thermal decomposition is conducted at a temperature of a least 300° C., which is the minimum temperature at which MgCl2 decomposes. Preferably, thermal decomposition is conducted at a temperature of at least 350° C. Due to energy costs, the temperature is preferably below 1000° C., more preferably below 800° C., still more preferably below 600° C. In addition, using a too high temperature for the thermal decomposition step is undesirable, because it will reduce the reactivity of the MgO formed, such that it is less suitable for use as a neutralizing agent in fermentation. For example, the temperature at which thermal decomposition is conducted may be 350-600° C. or 400-500° C. The temperature mentioned is the temperature of the gases as they are removed from the unit.

Thermal decomposition as applied in the present invention is preferably conducted at a pressure of 0.1-10 bar. However, the use of elevated pressure may be undesirable, because of an increased risk of corrosion due to the HCl not being able to condense. Preferably, thermal decomposition is conducted at atmospheric pressure, in particular when using a roaster, to avoid unnecessary energy costs and the need for expensive high pressure equipment. A pressure in the range of 0.9-1 bar may be preferred to prevent venting of HCl.

From the thermal decomposition step, MgO is withdrawn in solid form.

A HCl containing gas stream with a temperature of at least 300° C. is withdrawn from the thermal decomposition step and recycled to the preconcentrator step. The temperature of the HCl-containing gas stream provided to the preconcentrator is in the range specified above for the temperature during the thermohydrolysis step. The HCl concentration in the gas stream generally is in the range of 5-15 wt. %, in particular 7-12 wt. %. The HCl-containing gas stream generally comprises 20-50 wt. % of water, in particular 30-45 wt. %. Depending on the further composition, the HCl-containing gas stream generally comprises at least 25 wt. % of inert gas, in particular of inert gas selected from the group consisting of N2, CO2 and mixtures thereof (such as air). This may, e.g., result from the thermohydrolysis being conducted in the presence of inert gases, for example in the presence of air.

The inert gas concentration may be higher, e.g., at least 50 wt. In one embodiment, the gas feed may comprise 40-80 wt. % nitrogen gas. The gas feed may comprise up to 95 wt. % inert gas. In one embodiment a gas feed obtained in MgCl2 thermohydrolysis is used which comprises 40-50 wt. % N2, 0-5 wt. % O2 and 5-15 wt. % CO2.

The process according to the invention is illustrated with reference to the following figures, without being limited thereto or thereby.

FIG. 1 illustrates the basic steps of the method according to the invention. The magnesium chloride solution is provided through line (1) to evaporation step (2). Gaseous effluent comprising water and optionally organic compounds is withdrawn through line (3). The concentrated magnesium chloride solution is withdrawn through line (4) and provided to the preconcentrator (5). In preconcentrator (5) the magnesium chloride solution is contacted with a hot HCl-containing gas stream provided through line (6). The HCl-containing gas stream is withdrawn from the thermohydrolysis unit (7). A concentrated magnesium chloride solution is withdrawn from the preconcentrator (5) through line (8) and provided to the thermohydolysis unit (7). An HCl-containing gas stream with a decreased temperature is withdrawn from preconcentrator (5) though line (9). Solid magnesium oxide is withdrawn from the thermohydrolysis unit through line (10). The thermohydrolysis unit is provided with hot gas, e.g., combustion gas through line (11).

Figure 2:
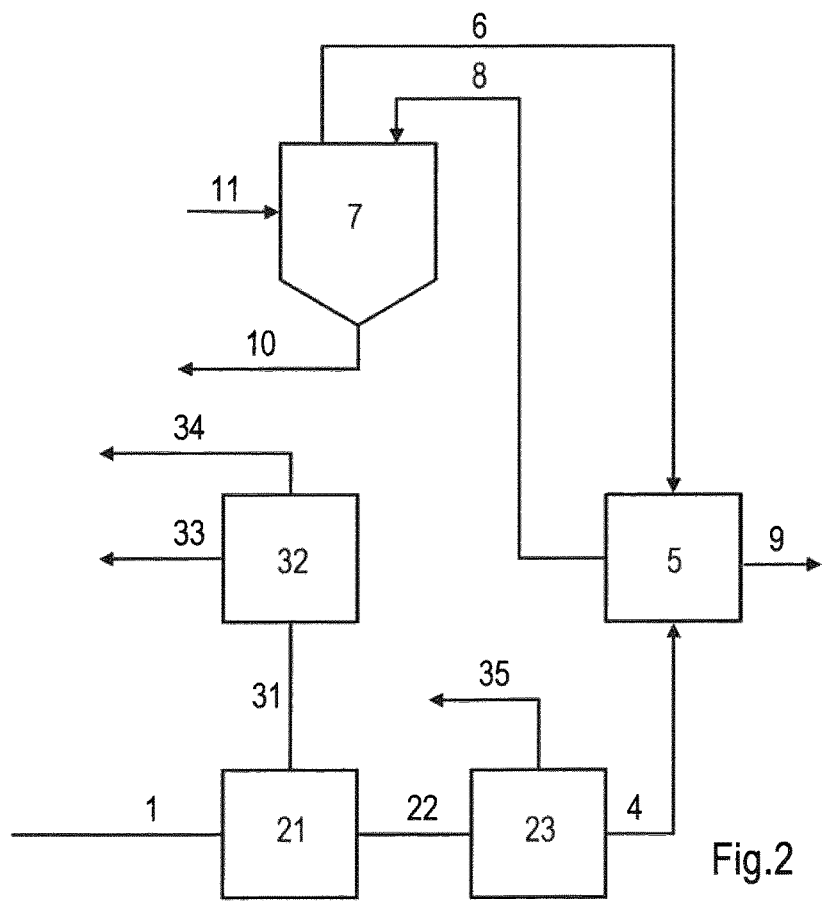
FIG. 2 is a variation of FIG. 1, illustrating a possible multi-stage separation step.

FIG. 2 is a variation on FIG. 1, illustrating a possible multi-stage separation step. In FIG. 2, the magnesium chloride solution is provided through line (1) to first evaporation stage (21). A stream (31) containing water and, in the case illustrated, organic components, is withdrawn from first separation step (21) and provided to separation step (32), where it is separated to form a water fraction, withdrawn through line (33) and an organic fraction, withdrawn through line (34). Separation step (32) can be carried out in manners known in the art, e.g., through condensation, phase separation, e.g., through decantation, or distillation. A suitable separation method will depend on the nature and amount of organic contaminants. It is within the scope of the skilled person to select a suitable separation method. A concentrated magnesium chloride solution is withdrawn from first separation stage (21), and provided to second separation stage (23). Water is evaporated, and withdrawn through line (35). It is noted that as the organic compounds are more volatile than water, the major part, if not all, of the organic compounds is removed from the system in the first evaporator. Therefore, provision of stream (35) to a separator will generally not be required.

In FIG. 2, two separation stages are shown. As will be evident to the skilled person, there may be a single second separation stage (23), aimed at water removal, but it is also possible to have more than one, e.g. 2-6 of these further water removal stages. For more information on how the evaporation step or stages may be carried out, reference is made to what is stated above.

As indicated earlier, the process according to the invention is particularly suitable for incorporation into a method for manufacturing organic components, in particular carboxylic acids using a fermentation step.

In one embodiment the present invention therefore pertains to a process comprising the steps of subjecting a carbon source to a fermentation step to form a carboxylic acid, which fermentation step comprises the steps of fermenting a carbon source by means of a microorganism in a fermentation broth to form carboxylic acid and neutralizing at least part of the carboxylic acid by adding a magnesium base selected from magnesium oxide and magnesium hydroxide, thereby obtaining a magnesium carboxylate, subjecting the magnesium carboxylate to an acidification step wherein the magnesium carboxylate is contacted with HCl in an aqueous environment to form an aqueous mixture comprising carboxylic acid and magnesium chloride, subjecting the aqueous mixture comprising carboxylic acid and magnesium chloride to a separation step, to form an effluent comprising carboxylic acid and a magnesium chloride solution, providing an aqueous solution comprising 5-25 wt. % of MgCl2 and optionally organic contaminants to an evaporation step, wherein water and, where present, organic components are evaporated, withdrawing an aqueous solution with a MgCl2 concentration of 25-35 wt. % from an evaporation step and providing it to a preconcentrator where it is contacted with a HCl containing gas stream with a temperature of at least 300° C., providing an aqueous solution with a MgCl2 concentration of 35-45 wt. % resulting from the preconcentrator to a thermohydrolysis reactor, the reactor being at a temperature of at least 300° C., withdrawing MgO from the thermohydrolysis reactor in solid form, and withdrawing a HCl containing gas stream from the thermohydrolysis reactor, said HCl-containing gas stream having a temperature of at least 300° C., providing the HCl-containing gas stream with a temperature of at least 300° C. to the preconcentrator, withdrawing a HCl-containing gas stream with a temperature of at most 150° C. from the preconcentrator.

The specific embodiments and preferences described above for the process according to the invention also apply to the integrated process.

In a preferred embodiment of the integrated process, the organic components evaporated during the evaporation step are recycled at least in part to the separation step.

In the integrated process, the organic components generally comprise carboxylic acid or carboxylate and/or organic compounds used in the separation step, e.g., extractants and/or solvents. Recycling of these compounds to the separation step has the combined advantage of increasing the yield of the process, where relevant reducing the amount of additional extractant added during the separation step, and reducing the amount of organics provided to the thermal decomposition step.

In a preferred embodiment of the integrated process, the magnesium oxide withdrawn from the thermohydrolysis reactor is recycled at least in part to the fermentation step. This can be done in the form of MgO or after conversion into magnesium hydroxide, e.g., by contacting the magnesium oxide with water to obtain a magnesium hydroxide slurry.

In a preferred embodiment of the integrated process, the HCl-containing gas stream derived from the preconcentrator is recycled at least in part to the acidification step. In one embodiment the HCl-containing gas stream is converted to a HCl solution by absorbing it in water, and the solution is recycled to the acidification step. In another embodiment, the HCl-containing gas stream is provided to the acidification step in gaseous form.

It is particularly preferred for the integrated process according to the invention to encompass a combination of the MgO recycling, the organic component recycling, and the HCl recycling described above.

The various steps in the integrated process which are additional to the processing of the magnesium chloride solution will be discussed below.

In the first step a carbon source is subjected to a fermentation step to form a carboxylic acid, which fermentation step comprises the steps of fermenting a carbon source by means of a micro-organism in a fermentation broth to form carboxylic acid and neutralizing at least part of the carboxylic acid by adding a magnesium base selected from magnesium oxide and magnesium hydroxide, thereby obtaining a magnesium carboxylate.

Fermentation processes for the manufacture of carboxylic acids are known in the art and require no further elucidation here. It is within the scope of the skilled person to select, using his common general knowledge, a suitable fermentation process, depending on the desired acid to be produced, the carbon source and the microorganism available.

The product of the fermentation process is a fermentation broth, which is an aqueous liquid comprising magnesium carboxylate, biomass, and optionally further components such as impurities like are sugars, proteins, and salts.

If so desired, the fermentation broth may be subjected to a biomass removal step, e.g., a filtration step, before further processing. This is generally preferred for improving product quality. Depending on the carboxylic acid produced, another intermediate step may be separation of solid reaction product, e.g., magnesium carboxylate, from the fermentation broth, before, after, or simultaneous with biomass removal, and optionally subjecting the magnesium carboxylate to a washing step.

Depending on the carboxylic acid produced, another intermediate step may be subjecting the fermentation broth to a concentration step to increase the concentration of magnesium carboxylate in the composition before acidification. This step may be carried out before, after, or simultaneous with biomass removal.

Other intermediate steps, e.g., purification steps, may be carried out as desired, as will be evident to the skilled person.

The next step in the integrated process according to the invention is subjecting the magnesium carboxylate to an acidification step, also sometimes indicated as acidulation step, wherein the magnesium carboxylate is contacted with HCl in an aqueous environment to form an aqueous mixture comprising carboxylic acid and magnesium chloride.

There are various ways in which this step can be effected. The acidulation step is typically conducted by bringing the carboxylate salt in contact with an acidic HCl solution. However, in some embodiments it may also be possible to contact the carboxylate salt with gaseous HCl.

The carboxylate salt may be in solid and/or dissolved form. In one embodiment, the carboxylate salt is provided in solid form. In this case, the acidulation step is conducted by bringing the carboxylate salt in contact with an acidic solution. The advantage of preparing the aqueous mixture from carboxylate salt in solid form is that very high carboxylic acid concentration can thus be obtained, such as concentration of at least 15 wt. %, in particular at least 25%, up to, e.g. 50 wt. %, or e.g. 40 wt. %.

The carboxylate salt may also be in dissolved form, typically as part of an aqueous solution. In this case, the acidulation step can be conducted by bringing the carboxylate salt in contact with an acidic solution or an acidic gas.

The acidulation step may also be conducted on a mixture of carboxylic acid and carboxylate salt. Such a mixture may for example be obtained in a low pH fermentation. The mixture may for example be an aqueous suspension.

When acidulation of the carboxylate salt is conducted by contacting it with an acidic HCl solution, it preferably has an acid concentration as high as possible. Such a high acid concentration will result in an aqueous mixture with a high carboxylic acid concentration, which is desirable. The acidic solution therefore comprises at least 5 wt. %, more preferably at least 10 wt. % and even more preferably at least 20 wt. % acid, based on the total weight of the acidic solution. Acidulation is typically conducted using an excess of acid. The excess is preferably small, such that the aqueous mixture obtained is not highly acidic, which may not be desirable in view of further processing such a mixture. For example, the excess of acid used may be such that the resulting aqueous mixture has a pH 2 or lower, preferably a pH of 0-1.

In case gaseous HCl is used, it may be contacted by bringing it in contact with a carboxylate solution or suspension. In particular, HCl gas may be blown through the solution or suspension.

Preferably, acidulation is conducted at a temperature of 75° C. or less. At higher temperatures, it becomes uneconomical to adapt equipment to the harsh conditions of an acidic environment at high temperatures.

The acidification step results in the formation of an aqueous liquid comprising carboxylic acid and magnesium chloride.

This aqueous liquid is subjected to a separation step, optionally after intermediate processing steps have been carried out such as a concentration step.

Suitable separation steps are known in the art. The nature of the step to be used depends on the nature and property of the acids.

Where the carboxylic acid is present in whole or in part as solid in the aqueous liquid, separation can take place using conventional solid-liquid separation methods such as filtration, centrifugation, etc.

Where the carboxylic acid is present in whole or in part as a separate organic phase in the aqueous liquid, separation can take place using conventional liquid-liquid separation methods, e.g., decantation, settling, centrifugation, use of plate separators, use of coalescers, and use of hydrocyclones. An extractant may be added to improve the separation efficiency. Combination of different methods and apparatus may also be used.

Where the carboxylic acid is present dissolved in the aqueous liquid, separation can take place using, e.g., extraction with a suitable extractant.

The process of the present invention is particularly attractive where the separation step encompasses the use of an extractant. It has been found that in this embodiment the magnesium chloride solution derived from the separation step may contain relatively large amounts of organic components as illustrated, e.g., by a VTOC of at least 1000 ppm (0.1 wt. %). Provision of these large amounts of organic components to the thermal decomposition step would lead to an undesirable HCl quality, the formation of undesirable products during thermal decomposition, and loss of extractant from the system. In the process according to the invention, these problems can be prevented. The use of a multiple stage separation step as described above is particularly preferred in this embodiment.

Where an extractant is present in the process according to the invention, the extractant, which may also be indicated as extraction agent is substantially not miscible with water. The use of an extractant results in the formation of a two-phase system during the separation step which comprises a liquid organic layer comprising extraction agent and carboxylic acid and an aqueous layer comprising dissolved magnesium chloride.

Examples of suitable extractants are aliphatic and aromatic hydrocarbons, such as alkanes and aromatic compounds, ketones, and ethers. Mixtures of various compounds may also be used.

Examples of suitable aliphatic alkanes are C5-C10 straight chain, branched, or cyclic alkanes, e.g., octane, hexane, cyclohexane, 2-ethyl-hexane, and heptane.

Examples of suitable aromatic compounds are C6-C10 aromatic compounds, e.g., toluene, xylenes, and ethylbenzene.

Examples of suitable ketones are C5+ ketones, more in particular C5-C8 ketones in the present invention. C5+ stands for ketones with at least 5 carbon atoms. The use of C9+ ketones is less preferred, The use of methyl-isobutyl-ketone (MIBK) has been found to be particularly attractive.

Examples of suitable ethers are C3-C6 ethers, e.g., methyl tert-butyl ether (MTBE) and diethyl ether (DEE). The extractant generally qualifies as VTOC in the context of the present specification.

The nature of the carboxylic acid manufactured is not critical to the integrated process according to the invention.

In one embodiment the carboxylic acid is a mono-, di- or tri-carboxylic acid comprising at least 2, but no more than 6 carbon atoms (C2-6 carboxylic acid). In one embodiment, the carboxylic acid is selected from the group consisting of lactic acid, succinic acid, propionic acid, 3-hydroxypropionic acid, 2-, 3-, and 4-hydroxybutyric acid, citric acid, fumaric acid, itaconic acid, adipic acid, acrylic acid, levulinic acid, maleic acid, 2,5-furandicarboxylic acid, mandelic acid, malic acid, and tartaric acid. Preferably, the carboxylic acid is selected from the group consisting of lactic acid, succinic acid, propionic acid, 3-hydroxypropionic acid, 2-, 3-, and 4-hydroxybutyric acid and citric acid.

In one embodiment, the carboxylic acid is selected from the mono-carboxylic acids with 2-6 carbon atoms. In one embodiment, the monocarboxylic acid with 2-6 carbon atoms does not contain hydroxyl-groups. Within this group, examples of suitable acids are propionic acid, acrylic acid, butyric acid, and valeric acid.

In another embodiment, the monocarboxylic acid contains at least one hydroxyl-group. Within this group, in one embodiment it may be preferred to select the acid from the group of lactic acid, glycolic acid, 3-hydroxypropionic acid, 2-, 3-, and 4-hydroxybutyric acid. In another embodiment within this group it may be preferred to select the acid from the group of glycolic acid, 3-hydroxypropionic acid, and 2-, 3-, and 4-hydroxybutyric acid. In a further embodiment it may be preferred for the acid to be lactic acid.

In another embodiment, the carboxylic acid is a polycarboxylic acid, more in particular a di- or tri-carboxylic acid comprising at least 2, but no more than 6 carbon atoms (C2-6 carboxylic acid). In one embodiment, the polycarboxylic acid is selected from the group consisting of succinic acid, citric acid, fumaric acid, itaconic acid, adipic acid, maleic acid, 2,5-furandicarboxylic acid, mandelic acid, malic acid, and tartaric acid. Preferably, the polycarboxylic acid is selected from the group consisting of succinic acid, citric acid, fumaric acid, itaconic acid, adipic acid, and 2,5-furandicarboxylic acid. The polycarboxylic acid may in particular be selected from succinic acid, fumaric acid, itaconic acid, and 2,5-furandicarboxylic acid.

Figure 3:
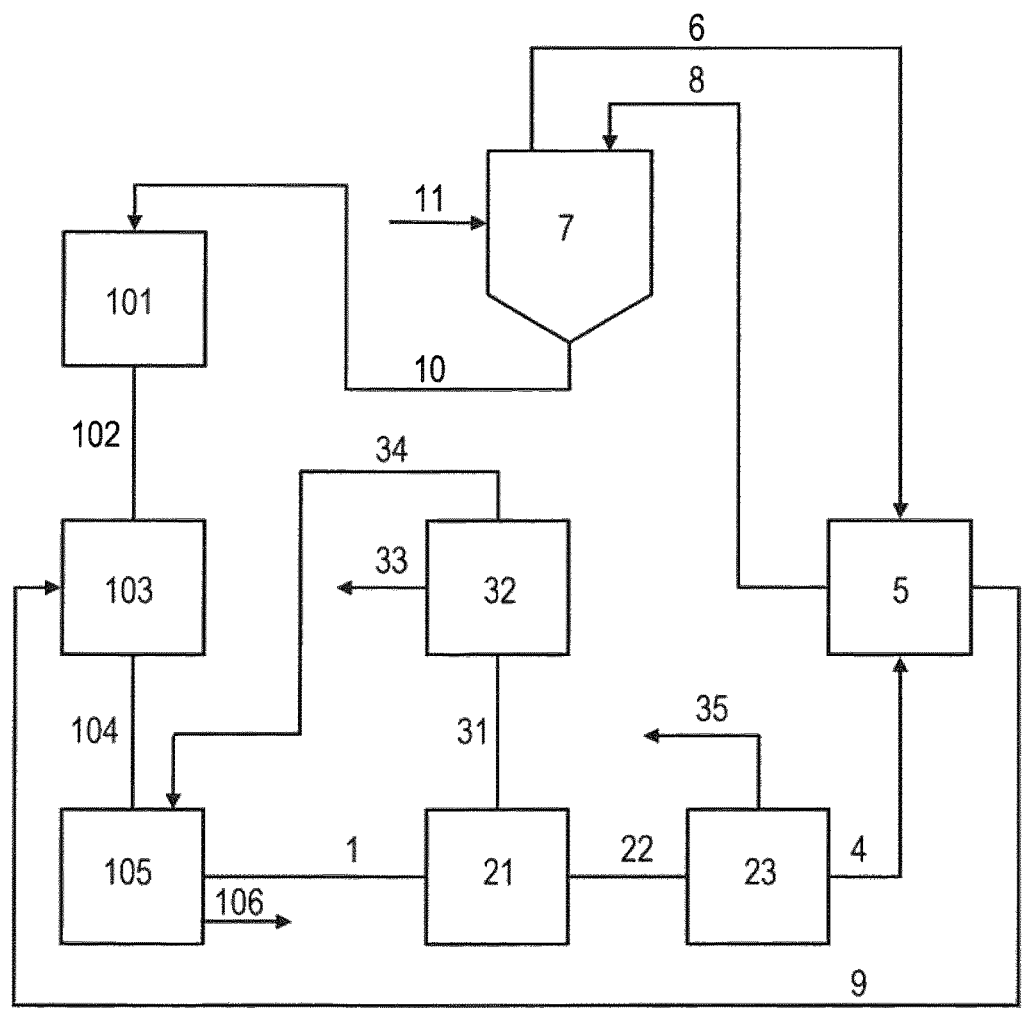
FIG. 3 illustrates an emobodiment of the integrated process according to the subject matter of the present application.

FIG. 3 illustrates an embodiment of the integrated process according to the invention. In FIG. 3, a fermentation step is carried out in fermentation reactor (101), which is provided with a carbon source and optionally further components such as nutrients through lines not shown. In the fermentation step a carbon source is fermented by means of a micro-organism in a fermentation broth to form carboxylic acid and neutralizing at least part of the carboxylic acid by adding a magnesium base, thereby obtaining a magnesium carboxylate. The magnesium base is added through line (10). The magnesium base is derived from MgO generated in the thermal decomposition step. The MgO may be provided as such, or after having been slurried in an aqueous liquid or converted to magnesium hydroxide in steps not shown. The fermentation broth comprising a magnesium carboxylate salt is provided to an acidification step (103) through line (102). Intermediate steps such as biomass removal or concentration may be carried out, but are not shown. In the acidification step (103) the magnesium carboxylate is contacted with HCl in an aqueous environment to form an aqueous mixture comprising carboxylic acid and magnesium chloride. The HCl is provided through line (9) and is derived from the preconcentrator (5). It may be provided in the form of a HCl-containing gas stream directly derived from preconcentrator (5). It may also be provided in the form of an aqueous solution obtained by absorbing the HCl-containing gas stream into an aqueous liquid (e.g., water). This would take place in an absorption step (not shown).

The aqueous mixture comprising carboxylic acid and magnesium chloride is provided to a separation step (105) through line (104). The separation step may be carried out as described above. The organic compounds obtained in separation step (32) are provided to separation step (105) through line (34). Where separation step (105) makes use of an extractant, this is provided through lines not shown. Separation step (105) results in an effluent comprising carboxylic acid and a magnesium chloride solution. The product carboxylic acid is withdrawn through line (106). The magnesium chloride solution is withdrawn through line (1), and processed further as described above in the context of FIG. 2).

The invention claimed is:

1. Method for processing magnesium chloride solutions comprising the steps of
providing an aqueous solution comprising 5-25 wt. % of magnesium chloride and organic contaminants to an evaporation step, wherein water and organic components are evaporated, wherein the product resulting from the evaporation step has a total organic compounds (TOC) which is at most 50% of the TOC of the aqueous solution provided to the evaporation step,
withdrawing an aqueous solution with a magnesium chloride concentration of 25-35 wt. % from the evaporation step and providing it to a preconcentrator where it is contacted with a HCl containing gas stream with a temperature of at least 300° C.,
providing an aqueous solution with a magnesium chloride concentration of 35-45 wt. % resulting from the preconcentrator to a thermohydrolysis reactor, the reactor being at a temperature of at least 300° C.,
withdrawing MgO from the thermohydrolysis reactor in solid form, and withdrawing a HCl containing gas stream from the thermohydrolysis reactor, said HCl-containing gas stream having a temperature of at least 300° C.,
providing the HCl-containing gas stream with a temperature of at least 300° C. to the preconcentrator,
withdrawing a HCl-containing gas stream with a temperature of at most 150° C. from the preconcentrator.

2. Method according to claim 1, wherein the aqueous solution comprising magnesium chloride has a TOC of at least 1000 ppm.

3. Method according to claim 1, wherein the product resulting from the evaporation step has a TOC which is at most 30% of the TOC of the aqueous solution provided to the evaporation step.

4. Method according to claim 1, wherein the product resulting from the evaporation step which is provided to the preconcentrator has a TOC of at most 1000 ppm.

5. Method according to claim 1, wherein the concentration increase effected during the evaporation step before the preconcentrator, defined as [magnesium chloride prec]-[magnesium chloride start], is between 30 and 5 wt. %.

6. Method according to claim 1, wherein the evaporation step is a single-stage evaporation step.

7. Method according to claim 1, wherein the evaporation step is a multiple-stage evaporation step.

8. Method according to claim 7, wherein in a first evaporation stage of the multiple-stage evaporation step, volatile organic compounds are removed, so that the concentrated product from the first evaporation stage has a total volatile organic compounds (VTOC) which is at most 50% of the VTOC of the aqueous solution provided to the first evaporation stage.

9. Method according to claim 7, wherein steam is withdrawn from the first evaporation stage and provided as heating liquid to a further evaporation stage.

10. Method according to claim 9, wherein the multiple-stage evaporation is carried out in a multiple-effect evaporator.

11. Method according to claim 1, wherein vapor-compression evaporation is used in the evaporation step or in one or more stages thereof.

12. Method according to claim 1, wherein the magnesium chloride solution is derived from a process comprising
subjecting a carbon source to a fermentation step to form a carboxylic acid, which fermentation step comprises the steps of fermenting a carbon source by means of a micro-organism in a fermentation broth to form carboxylic acid and neutralizing at least part of the carboxylic acid by adding a magnesium base selected from magnesium oxide and magnesium hydroxide, thereby obtaining a magnesium carboxylate,
subjecting the magnesium carboxylate to an acidification step wherein the magnesium carboxylate is contacted with HCl in an aqueous environment to form an aqueous mixture comprising carboxylic acid and magnesium chloride,
subjecting the aqueous mixture comprising carboxylic acid and magnesium chloride to a separation step, to form (1) an effluent comprising carboxylic acid and (2) a magnesium chloride solution.

13. Method according to claim 12 further comprising
recycling the organic components evaporated during the evaporation step at least in part to the separation step, and/or
recycling the magnesium oxide withdrawn from the thermohydrolysis reactor at least in part to the fermentation step, and/or
recycling the HCl-containing gas stream derived from the preconcentrator at least in part to the acidification step.

14. Method according to claim 12, wherein the method further comprises
recycling the organic components evaporated during the evaporation step at least in part to the separation step, and
recycling the magnesium oxide withdrawn from the thermohydrolysis reactor at least in part to the fermentation step, and
recycling the HCl-containing gas stream derived from the preconcentrator at least in part to the acidification step.

15. Method according to claim 12, wherein the separation step encompasses an extraction step, wherein use is made of an organic extractant.

16. Method for manufacturing a carboxylic acid comprising
subjecting a carbon source to a fermentation step to form a carboxylic acid, which fermentation step comprises the steps of fermenting a carbon source by means of a micro-organism in a fermentation broth to form carboxylic acid and neutralizing at least part of the carboxylic acid by adding a magnesium base selected from magnesium oxide and magnesium hydroxide, thereby obtaining a magnesium carboxylate,
subjecting the magnesium carboxylate to an acidification step wherein the magnesium carboxylate is contacted with HCl in an aqueous environment to form an aqueous mixture comprising carboxylic acid and magnesium chloride,
subjecting the aqueous mixture comprising carboxylic acid and magnesium chloride to a separation step, to form (1) an effluent comprising carboxylic acid and (2) a magnesium chloride solution, providing an aqueous solution comprising 5-25 wt. % of magnesium chloride and organic contaminants to an evaporation step, wherein water and organic components are evaporated, wherein the product resulting from the evaporation step has a total organic compounds (TOC) which is at most 50% of the TOC of the aqueous solution provided to the evaporation step, withdrawing an aqueous solution with a magnesium chloride concentration of 25-35 wt. % from the evaporation step and providing it to a preconcentrator where it is contacted with a HCl containing gas stream with a temperature of at least 300° C., providing an aqueous solution with a magnesium chloride concentration of 35-45 wt. % resulting from the preconcentrator to a thermohydrolysis reactor, the reactor being at a temperature of at least 300° C., withdrawing MgO from the thermohydrolysis reactor in solid form, and withdrawing a HCl containing gas stream from the thermohydrolysis reactor, said HCl-containing gas stream having a temperature of at least 300° C., providing the HCl-containing gas stream with a temperature of at least 300° C. to the preconcentrator, withdrawing a HCl-containing gas stream with a temperature of at most 150° C. from the preconcentrator, wherein the carboxylic acid is derived from the effluent comprising carboxylic acid.

* * * * *